(12) United States Patent
Kipp et al.

(10) Patent No.: US 8,333,959 B2
(45) Date of Patent: *Dec. 18, 2012

(54) EX-VIVO APPLICATION OF SOLID MICROPARTICULATE THERAPEUTIC AGENTS

(75) Inventors: James E. Kipp, Wauconda, IL (US); Barrett E. Rabinow, Skokie, IL (US)

(73) Assignees: Baxter International Inc., Deerfield, IL (US); Baxter Healthcare S.A., Glattpark (Opfikon) (CH); Board of Regents of the University of Nebraska by and Behalf of the University of Nebraska Medical Center, Omaha, NE (US)

( * ) Notice: Subject to any disclaimer, the term of this patent is extended or adjusted under 35 U.S.C. 154(b) by 415 days.

This patent is subject to a terminal disclaimer.

(21) Appl. No.: 11/148,453

(22) Filed: Jun. 9, 2005

(65) Prior Publication Data

US 2005/0276861 A1  Dec. 15, 2005

Related U.S. Application Data

(60) Provisional application No. 60/579,891, filed on Jun. 15, 2004.

(51) Int. Cl.
  *A01N 63/00* (2006.01)
(52) U.S. Cl. ................ 424/93.7; 424/93.2; 435/325
(58) Field of Classification Search .................. None
  See application file for complete search history.

(56) References Cited

U.S. PATENT DOCUMENTS

| | | | |
|---|---|---|---|
| 4,224,313 A | 9/1980 | Zimmermann et al. | |
| 4,269,826 A | 5/1981 | Zimmermann et al. | |
| 4,289,756 A | 9/1981 | Zimmermann et al. | |
| 4,608,278 A | 8/1986 | Frank et al. | |
| 4,826,689 A | 5/1989 | Violanto | |
| 4,973,465 A | 11/1990 | Domb | |
| 4,997,454 A | 3/1991 | Violante et al. | |
| 5,091,188 A | 2/1992 | Haynes | |
| 5,100,591 A | 3/1992 | Leclef et al. | |
| 5,118,528 A | 6/1992 | Fessi et al. | |
| 5,145,684 A | 9/1992 | Liversidge et al. | |
| 5,188,837 A | 2/1993 | Domb | |
| 5,560,932 A | 10/1996 | Bagchi et al. | |
| 5,662,883 A | 9/1997 | Bagchi et al. | |
| 5,665,331 A | 9/1997 | Bagchi et al. | |
| 5,716,642 A | 2/1998 | Bagchi et al. | |
| 5,720,551 A | 2/1998 | Shechter | |
| 5,780,062 A | 7/1998 | Frank et al. | |
| 5,981,719 A | 11/1999 | Woiszwillo et al. | |
| 6,045,829 A | 4/2000 | Liversidge et al. | |
| 6,068,858 A | 5/2000 | Liversidge et al. | |
| 6,090,925 A | 7/2000 | Woiszwillo et al. | |
| 6,143,211 A | 11/2000 | Mathiowitz et al. | |
| 6,160,015 A * | 12/2000 | Ratner ........................ 514/542 |
| 6,235,224 B1 | 5/2001 | Mathiowitz et al. | |
| 6,268,053 B1 | 7/2001 | Woiszwillo et al. | |
| 6,331,299 B1 | 12/2001 | Rothman et al. | |
| 6,455,073 B1 | 9/2002 | Meredith et al. | |
| 6,458,387 B1 | 10/2002 | Scott et al. | |
| 6,607,784 B2 | 8/2003 | Kipp et al. | |
| 6,616,869 B2 | 9/2003 | Mathiowitz et al. | |
| 6,632,671 B2 | 10/2003 | Unger | |
| 6,638,621 B2 | 10/2003 | Anderson | |
| 6,645,464 B1 | 11/2003 | Hainfeld | |
| 6,790,455 B2 | 9/2004 | Chu et al. | |
| 6,835,396 B2 | 12/2004 | Brynjelsen et al. | |
| 6,869,617 B2 | 3/2005 | Kipp et al. | |
| 6,884,436 B2 | 4/2005 | Kipp et al. | |
| 6,902,743 B1 | 6/2005 | Setterstrom et al. | |

(Continued)

FOREIGN PATENT DOCUMENTS

EP  1952825  8/2008

(Continued)

OTHER PUBLICATIONS

Packer R.J. et al. "Plexiform neurofibromas in NF1: toward biologic-based therapy", Neurology, May 2002, 58: 1461-1470, entire document.*

Dilworth J.T. et al. "Molecular targets for emerging anti-tumor tumor therapies for neurofibromatosis type 1", Biochemical Pharmacology, 2006, 72: 1485-1492, entire document.*

Korf B.R. "Determination of end points for treatment of neurofibromatosis 1", J. Child Neurol., Aug. 2002, 17(8): 642-645, entire document.*

MacCollin M. et al. "Establishing priorities in neurofibromatosis research: a workshop summary", Genetics in Medicine, May/Jun. 2001, 3(3): 212-217, entire document.*

(Continued)

*Primary Examiner* — Jon P Weber
*Assistant Examiner* — Satyendra Singh
(74) *Attorney, Agent, or Firm* — Marshall, Gerstein & Borun LLP

(57) ABSTRACT

The present invention is concerned with a method of preparing and delivering small particles of a pharmaceutically active material to a mammalian subject for treating diseases or disorders. A preferred embodiment entails: (i) the collection of tissue cells from an animal donor, (ii) selective or non-selective growth of these cells in a cell culture medium to which is added solid particles of a therapeutically active compound, mostly free of a drug carrier (about 10% or less, by weight), and having an average particle size of less than about 100 microns, (iii) contacting the cells in the cell culture medium with the solid particles of therapeutically active compound causing the particles to be taken up by the cells into either the intracellular compartment of the cultured cells, attachment of the active compound as particles to the periphery of such cells, or a combination of intracellular uptake and attachment to the cell surface, (iv) optionally, isolation and/or resuspension of the cells prepared in steps i through iii, (v) administering the cells to the mammalian subject. The pharmaceutically active material can be administered intravenously, intramuscularly, subcutaneously, intradermally, intra-articularly, intrathecally, epidurally, intracerebrally, via buccal route, rectally, topically, transdermally, orally, intranasally, via pulmonary route, intraperitoneally, or combinations thereof. After administration, the loaded cells transport the pharmaceutical composition as particles.

22 Claims, No Drawings

U.S. PATENT DOCUMENTS

| | | |
|---|---|---|
| 2001/0042932 A1 | 11/2001 | Mathiowitz et al. |
| 2002/0127278 A1 | 9/2002 | Kipp et al. |
| 2002/0164694 A1 | 11/2002 | Moore et al. |
| 2002/0168402 A1 | 11/2002 | Kipp et al. |
| 2002/0176935 A1 | 11/2002 | Kipp et al. |
| 2003/0022846 A1 | 1/2003 | Meredith et al. |
| 2003/0054035 A1 | 3/2003 | Chu et al. |
| 2003/0059472 A1 | 3/2003 | Brynjelsen et al. |
| 2003/0092069 A1 | 5/2003 | Kuroda et al. |
| 2003/0206959 A9 | 11/2003 | Kipp et al. |
| 2003/0211083 A1 | 11/2003 | Vogel et al. |
| 2004/0022861 A1 | 2/2004 | Williams et al. |
| 2004/0043077 A1 | 3/2004 | Brown |
| 2004/0062756 A1 | 4/2004 | Humeau et al. |
| 2005/0037083 A1 | 2/2005 | Brynjelsen et al. |
| 2005/0084456 A1 | 4/2005 | Tang et al. |
| 2005/0112141 A1 | 5/2005 | Terman |
| 2006/0073199 A1 | 4/2006 | Chaubal et al. |

FOREIGN PATENT DOCUMENTS

| | | |
|---|---|---|
| RU | 2003108736 | 7/2006 |
| WO | WO-92/11846 | 7/1992 |
| WO | WO-92/17214 | 10/1992 |
| WO | WO-94/07999 | 4/1994 |
| WO | WO 97/14407 | 4/1997 |
| WO | WO-98/01162 | 1/1998 |
| WO | WO-98/47492 | 10/1998 |
| WO | WO-99/13054 | 3/1999 |
| WO | WO-00/64954 | 11/2000 |
| WO | WO-01/58431 | 8/2001 |
| WO | WO-01/82899 A2 | 11/2001 |
| WO | WO-02/055059 | 7/2002 |
| WO | WO-02/060416 | 8/2002 |
| WO | WO-02/082074 | 10/2002 |
| WO | WO-2004/035768 | 4/2004 |
| WO | WO-2004/110270 | 12/2004 |
| WO | WO-2004/112747 | 12/2004 |
| WO | WO-2004/112747 A2 | 12/2004 |
| WO | WO-2005/016246 | 2/2005 |
| WO | WO-2005/059118 | 6/2005 |
| WO | WO-2005/072706 | 8/2005 |
| WO | WO-2005/079854 | 9/2005 |
| WO | WO-2005/123907 | 12/2005 |
| WO | WO-2007/048326 | 5/2007 |

OTHER PUBLICATIONS

Riccardi V.M. "The genetic predisposition to and histogenesis of neurofibromas and neurofibrosarcoma in neurofibromatosis Type 1", Neurosurg. Focus, Jun. 2007, 22(6): E3, pp. 1-11, entire document.*

Moffat D.A. et al. "Management strategies in neurofibromatosis type 2", Eur. Arch. Otorhinolaryngol., 2003, 260: 12-18, entire document.*

Hanemann C.O. "Magic but treatable? Tumours due to loss of Merlin", Brain, 2007, pp. 1-10, entire document.*

Mishra P.R. and Jain N.K. Surface modified methotrexate loaded erythrocytes for enhanced macrophage uptake, Journal of Drug Targeting, 2000, vol. 8, No. 4, pp. 217-224.*

Mishra P.R. et al. Engineered human erythrocytes as carriers for Ciprofloxacin, Drug Delivery, 1996, vol. 3, pp. 239-244.*

D'Souza M. J. and DeSouza P. Site specific microencapsulated drug targeting strategies—liver and gastro-intestinal tract targeting, Advanced Drug Delivery Reviews, 1995, vol. 17, pp. 247-254.*

Kreuter J. Nanoparticulate systems for brain delivery of drugs, Advanced Drug Delivery Reviews, 2001, vol. 47, pp. 65-81.*

U2—Coester C. et al. Preparation of avidin-labelled gelatin nanoparticles as carriers for biotinylated peptide nucleic acid (PNA), International Journal of Pharmaceutics, 2000, vol. 196, pp. 147-149.*

Munerati M. et al. Macrophages loaded with doxorubicin by ATP-mediated permeabilization: Potential carriers for antitumor therapy, Biochimica et Biophysica Acta, 1994, vol. 1224, pp. 269-276.*

Soma C.E. et al. Investigation of the role of macrophages on the cytotoxicity of doxorubicin and doxorubicin-loaded nanoparticles on M5076 cells in vitro, Journal of Controlled Release, 2000, vol. 68, pp. 283-289.*

International Search Report for Application No. PCT/US2005/022992 (mailing date Jul. 12, 2007).

Von Briesen et al., "Controlled release of antiretroviral drugs," *AIDS Rev.*, 2:31-38 (2000).

Written Opinion of the International Searching Authority for Application No. PCT/US2005/022992 (mailing date Jul. 12, 2007).

US 5,849,884, 12/1998, Woiszwillo et al. (withdrawn).

Bender et al., Antimicrobial Agents and Chemotherapy, Jun. 1996, vol. 40(6), pp. 1467-1471, United Kingdom.

Ozawa et al., Annu Rev Pharmacol Toxicol, 2000, vol. 40, pp. 295-317.

Watts et al., J of Cell Sci, 1992, vol. 103(1), pp. 1-8, Great Britain.

Zarnitsyn et al., Ultrasound in Med & Biol, 2004, vol. 30, No. 4, pp. 527-538, USA.

Aquaro et al., "Macrophages and HIV infection: therapeutical approaches toward this strategic virus reservoir," *Antiviral Research*, 55:209-225 (2002).

Crowe et al., "The contribution of monocyte infection and trafficking to viral persistence, and maintenance of the viral reservoir in HIV infection," *Journal of Leukocyte Biology*, 74:635-641 (2003).

Fischer-Smith et al., "CNS invasion by CD14+/CD16+ peripheral blood-derived monocytes in HIV dementia: perivascular accumulation and reservoir of HIV infection," *Journal of Neurovirology*, 7:528-541 (2001).

Heiati et al., "Soild lipid nanoparticles as drug carriers: II. Plasma stability and biodistribution of solid lipid nanoparticles containging the lipophilic prodrug 3'-azido-3'-deoxythymidine palmitate in mice," *Int. J. Pharmaceutics*, 174:71-80 (1998).

Igarashi et al., "Macrophage are the principal reservoir and sustain high virus loads in rhesus macaques after the depletion of CD4+ T cells by a highly pathogenic simian immunodeficiency virus/HIV type 1 chimera (SHIV): implications for HIV-1 infections of humans," *Proc. Nat. Acad. Sci, USA*, 98:658-663 (2001).

Kinman et al., "Lipid-drug association enhanced HIV-1 protease inhibitor indinavir localization in lymphoid tissues and viral load reduction: a proof of concept study in HIV-2287-infected macaques," *J. Acquir. Immune Defic. Syndr.*, 34:387-397 (2003).

Limoges et al., "Sustained antiretroviral activity of indinavir nanosuspensions in primary monocyte-derived macrophages," poster presentation, 11th Conference on Retroviruses and Opportunistic Infections, Feb. 8-11, 2004.

Lobenberg et al., "Macrophage targeting of azidothymidine: a promising strategy for AIDS therapy," *AIDS Res. Hum. Retroviruses*, 12:1709-1715 (1996).

Lobenberg et al., "Body distrbuton of azidothymidine bound to hexyl-cyanoacryate nanoparticles after i.v. injection to rats," *J. Control. Release*, 50:21-30 (1998).

Moghimi et al., "Long-circulating and target-specific nanoparticles: theory to practice," *Pharmacological Reviews*, 53:283-318 (2001).

Nesbit et al., "In vitro and animal models of human immunodeficiency virus infection of the central nervous system," *Clinical and Diagnostic Laboratory Immunology*, 9:515-524 (2002).

Nottet et al., "HIV-1 entry into brain: mechanisms for the infiltration of HIV-1-infected macrophages across the blood-brain barrier," p. 55, in Gendelman (ed.) et al., *The Neurology of AIDS*, New York: Hodder Arnold Publication (1997).

Perno et al., "Relative potency of protease inhibitors in monocytes/macrophages acutely and chronically infected with human immunodeficiency virus," *The Journal of Infectious Diseases*, 178:413-422 (1998).

Sawchuk et al., "Investigation of distribution, transport and uptake of anti-HIV drugs to the central nervous system," *Advanced Drug Delivery Reviews*, 39:5-31 (1999).

Solas et al., "Discrepancies between protease inhibitor concentrations and viral load in reservoirs and sanctuary sites in human immunodeficiency virus-infected patients," *Antimicrobial Agents and Chemotherapy*, 47:238-243 (2003).

Dou et al., Macrophage delivery of nanoformulated antiretroviral drug to the brain in a murine model of neuroAIDS, *J. Immunol.*, 183:611-9 (2009).

Dou et al., Laboratory investigations for the morphologic, pharmacokinetic, and anti-retroviral properties of indinavir nanoparticles in human monocyte-derived macrophages, *Virology*, 358:148-58 (2007).

Gorantla et al., Quantitative magnetic resonance and SPECT imaging for macrophage tissue migration and nanoformulated drug delivery, *J. Leukocyte Biol.*, 80:1165-74 (2006).

Kingsley et al., Nanotechnology: a focus on nanoparticles as a drug delivery system, *J. Neuroimmune Pharmacol.*, 1:340-50 (2006).

Liu et al., Ingress of blood-borne macrophages across the blood-brain barrier in murine HIV-1 encephalitis, *J. Neuroimmunol.*, 200:41-52 (2008).

Nowacek et al., NanoART synthesis, characterization, uptake, release and toxicology for human monocyte-macrophage drug delivery, *Nanomedicine*, 4:903-17 (2009).

Dou et al., Development of a macrophage-based nanoparticles platform for antiretroviral drug delivery, *Blood*, 108:2827-35 (2006).

Ginsburg et al., Role of leukocyte factors and cationic polyelectrolytes in phagocytosis of group A streptococci and *Candida albicans* by neutrophils, macrophages, fibroblasts and epithelial cells: modulation by anionic polyelectrolytes in relation to pathogenesis of chronic inflammation, Inflammation, 5:289-312 (1981).

Issekutz et al., The in vivo quantitation and kinetics of monocyte migration into acute inflammatory tissue, *Am. J. Pathol.*, 103:47-55 (1981).

Allen et al., "Critical evaluation of acute cardiopulmonary toxicity of microspheres," *J. Nucl. Med.*, 19:1204-1208 (1987).

Davis et al., "Pulmonary perfusion imaging: acute toxicity and safety factors as a function of particle size," *J. Nucl. Med.*, 19:1209-13 (1978).

Schroeder et al., "Physiological effects of subvisible microspheres administered intravenously to beagle dogs," *J. Pharm. Sci.*, 67:508-13 (1978).

Yokel et al., "Acute toxicity of latex microspheres," *Toxicol. Lett.*, 9:165-70 (1981).

Thiele et al., Competitive adsorption of serum proteins at microparticles affects phagocytosis by dendritic cells, Biomaterials, 24:1409-18 (2003).

\* cited by examiner

# EX-VIVO APPLICATION OF SOLID MICROPARTICULATE THERAPEUTIC AGENTS

CROSS-REFERENCE TO RELATED APPLICATIONS

This application claims priority to U.S. Provisional Patent Application Ser. No. 60/579,891, filed Jun. 15, 2004.

FEDERALLY SPONSORED RESEARCH OR DEVELOPMENT

Not Applicable.

BACKGROUND OF THE INVENTION

1. Technical Field

The present invention is concerned with the ex vivo, cell-mediated, delivery of pharmaceutically active material to a subject. The pharmaceutically active material is initially prepared as a microparticulate, which is engulfed or adsorbed by cells. The cells are then administered to a subject.

2. Background Art

The ex-vivo delivery of pharmaceutically active compounds has been successfully accomplished in several therapeutic areas, particularly in gene delivery. For ex-vivo delivery, cells are removed from the patient, modified outside the body, and reimplanted. In-vivo delivery consists of administering the pharmaceutical agent directly into the body, including intravenous, intramuscular, subcutaneous, intradermal, intra-articular, intrathecal, epidural, intracerebral, bucchal, rectal, topical, transdermal, oral, intranasal, pulmonary, and intraperitoneal administration. In-vivo delivery of genetic material is, at first glance simpler, but raises significant safety concerns. Ex-vivo delivery is more complicated but permits safety testing before the genetically modified cells are administered. Candidate genetic material includes encoding for secreted factors that could have broad applications ranging from treatment of inherited single-gene deficiencies to acquired disorders of the vasculature or cancer. Myoblasts have been recently transfected via retroviral vectors (Ozawa C R, Springer M L, Blau H M, A novel means of drug delivery: myoblast-mediated gene therapy and regulatable retroviral vectors. *Annu Rev Pharmacol Toxicol.* 2000; volume 40, pages 295-317).

In the area of pharmaceutical delivery of small molecules, Bender et al. disclose the treatment of HIV-infected monocytes/macrophages with polyhexylcyanoacrylate nanoparticles loaded with either the nucleoside analog zalcitabine (2',3'-dideoxycytidine), or saquinavir, a protease inhibitor (Bender et al., Efficiency of Nanoparticles as a Carrier System for Antiviral Agents in Human Immunodeficiency Virus-Infected Human Monocytes/Macrophases In Vitro, Antimicrobial Agents and Chemotherapy, June 1996, volume 40(6), p. 1467-1471). The polyhexylcyanoacrylate nanoparticles were prepared by emulsion polymerization and tested in-vitro for antiviral activity in primary human monocytes/macrophages. An aqueous solution of saquinavir showed little antiviral activity in HIV-infected macrophages, whereas the nanoparticulate formulation demonstrated significant antiviral activity at one-tenth the solution concentration. At a concentration of 100 nM, saquinavir in solution was completely inactive in chronically HIV-infected macrophages, but when bound to nanoparticles it caused a 35% decrease in viral antigen production. In this study, the drug was entrained in a polymer (polyhexylcyanoacrylate) matrix. Preparation of pure, solid drug nanoparticles for delivery to macrophages was not disclosed. Particles were only delivered to macrophages in-vitro and did not contemplate drug delivery by administering nanoparticle-treated cells that are capable of transporting the drug.

U.S. Pat. No. 4,973,465 (Baurain et al.) and U.S. Pat. No. 5,100,591 (Leclef et al.) discloses lipid microparticles of nystatin, amphoterin B and other anti-fungal compounds, potentially having enhanced targeting for macrophages.

The present invention overcomes the disadvantages of the prior art by providing pharmaceutical compositions comprising solid pharmaceutical agents in an ex-vivo drug delivery method. The advantage to this approach over the use of an adjunct (i.e., direct patient dosing formulation) matrix, is that high drug loading is achieved and a high burst of drug may be delivered. As part of this invention we disclose the ex-vivo application of solid submicron particles that are mostly free of a carrier matrix and consisting only of solid drug with stabilizing surface-active ingredients. The solid particulate is contacted with cells capable of engulfing the particles or in which the particles are capable of attachment to the outer surfaces of the cells. Several therapeutic areas are appropriate for this ex-vivo technology: treatment of bacterial, viral, and fungal infections, neoplasms, lysosomal storage disorders, autoimmune disorders, and metabolic disorders. Gene delivery and delivery of antisense oligonucleotides are also disclosed.

Ex-vivo delivery of solid nanoparticles, particularly particles of essentially pure active agent, can provide many advantages in several therapeutic areas. For example, in gene therapy, vectors are typically used that can either be viral or nonviral. To their advantage, viruses offer strong specificity and high transfection efficiency via the virus's natural mechanism for delivering DNA into the cell. Having the gene expressed in-vivo can also induce unintended, fatal consequences, particularly if undesired expression of the viral genetic material occurs. Nonviral approaches, on the other hand, though less toxic, are relatively inefficient and nonspecific. However, the non-viral vectors rely on carrier vesicles for the nucleic acid. U.S. Patent Publication No. US 2003/0092069 attempts to remedy the non-specific delivery of genes, in vivo, in disclosing the site specific delivery of genes via a hollow nanoparticle. More specifically, the '069 publication discloses the use of a biorecognition molecule (L protein of hepatitis B virus) for the delivery of a protein to a hepatocyte.

Pharmaceutical agents may be delivered to phagocytizing cells in ex-vivo culture by adding a solution. However, most of the drug may not sufficiently concentrate in cells when influx relies on molecular diffusion of drug solute across membranes. This inefficient utilization of drug may require extracellular perfusion of higher drug concentrations that can produce cytotoxic effects in culture. More efficient delivery of the drug may be realized by leveraging the ability of phagocytes (e.g., macrophages, monocytes, reticulocytes, eosinophils, basophils, neutrophils, and dendritic cells, among others) to engulf particles.

The present invention overcomes the foregoing limitations by delivering a substantially carrier-free, pharmaceutical agent microparticulate, by cells that are capable of engulfing the microparticulate, or by adsorbing the pharmaceutical agent microparticulate on the cell surface, and which upon delivery of the loaded cells to the patient is capable of reaching the target tissues.

SUMMARY OF THE INVENTION

The present invention provides a method for delivering a pharmaceutical composition to target cells of a mammalian subject by cellular transport. More specifically, the present invention method involves the: (1) the collection of tissue cells from a mammalian donor, (2) selective or non-selective growth of these cells in a cell culture medium to which is added a pharmaceutical composition comprising solid particles of a therapeutically active compound, preferably, mostly free of a drug carrier (about 10% or less, by weight), with the purpose of delivering the active compound to either the intracellular compartment of the cultured cells, attachment of the active agent to the periphery of such cells, or a combination of intracellular uptake and attachment to the cell surface, (3) optionally, isolation and/or resuspension of the cells prepared in steps 1 and 2, and (4) administration of the cellular suspension prepared in steps 1 through 3 into a mammal.

After isolation from the mammalian subject, the cells are placed in contact with pharmaceutical composition comprising particles of pharmaceutical agents. The cells may take up the particles through phagocytosis or adsorption of the particle onto the surface of the cell, or by site-specific delivery (e.g., use of a biorecognition molecule in conjunction with a lipid or other hollow nanoparticle). Phagocytic cells include, but are not limited to, macrophages, monocytes, granulocytes, neutrophils, basophils, eosinophils and dendritic cells. Any other type of cell that will engulf or adsorb a microparticle of drug can be used in the present invention. Such other cells to be harvested and dosed ex vivo include, but are not limited to, red blood cells, muscle cells, bone marrow and bone cells, vascular cells, organ tissue cells and neuronal cells. In a preferred form of the invention, during contact with the cells, the particles are at a concentration higher than the thermodynamic saturation solubility thereby allowing the particles to remain in particulate form during uptake and subsequent delivery to target somatic tissues by the cells.

The loaded cells can be administered by many routes, including intravenous, intramuscular, subcutaneous, intradermal, intra-articular, intrathecal, epidural, intracerebral, intraperitoneal, intra-ophthalmic, retro-orbital and the like. The loaded cells may be infused, either intermittantly or continuously, or injected by syringe.

In another preferred embodiment, the method comprises the steps of providing a dispersion of the pharmaceutical composition as particles having an average particle size of less than about 100 microns (preferably, less than 10 microns) and administering the dispersion directly to the mammalian subject for delivery to target tissues of a portion of the pharmaceutical composition, by reinfused cells capable of reaching the target tissue. The pharmaceutical composition utilized in these processes can be prepared as small solid particles and can be a therapeutic agent or a diagnostic agent. The therapeutic agents can include any agents used to treat mammalian diseases, such as but not limited to agents for the treatment of bacterial, viral, and fungal infections, neoplasms, lysosomal storage disorders, autoimmune disorders, inflammatory, and metabolic disorders. Therapeutic agents for gene delivery and delivery of antisense oligonucleotides (ATO) are also disclosed.

There are numerous advantages of ex-vivo drug delivery over in vivo administration. For example, by delivering solid drug particles that are associated (e.g., engulfed or adsorbed on the cell surface) with cells, the drug particles can be transported to sites of infection. Phagocytosis is carried out by white blood cells, mainly macrophages, neutrophils, and eosinophils. Neutrophils predominate early in infection or inflammation, followed by wandering macrophages that originate from monocytes that leave the blood vasculature and enter infected tissue. Fixed macrophages (histiocytes) abound in the liver, nervous system, lungs, lymph nodes, bone marrow, and several other tissues. Tissues that are most affected by bacterial, viral or fungal pathogens and which are inflamed can be targeted by delivery of drug-loaded cells (granulocytes, for example) having a propensity to be directed to these inflammation sites by chemotaxis. The pharmaceutical agent is released from these cells in a region of inflammation with high populations of pathogens. Or, the pharmaceutical agent may be an anti-inflammatory drug (steroid, for example), in which case the drug is released in the region where it is therapeutically most needed.

Excessive liver metabolism of drugs can be avoided and the cost of therapy can be reduced through this invention. This concept is yet further extended in this invention to cover delivery of small, solid particles to any repository for phagocytic cells, recognizing that phagocytes, particularly macrophages, are pervasive in nearly all connective tissues throughout the body. Macrophages can be divided into normal and inflammatory macrophages. Normal macrophages include those histiocytes that reside in connective tissue, Kupffer's cells of the liver, alveolar macrophages within the lung, free and fixed macrophages within the lymph nodes, spleen (free and fixed macrophages), bone marrow (fixed macrophages), serous fluids (pleural and peritoneal macrophages), skin (histiocytes, Langerhans's cells) and in other tissues. The macrophage population in a specific tissue may be maintained by several competing processes: monocyte influx from the blood, local proliferation from progenitor cells, and turnover. Inflammatory macrophages are present in extracellular fluids.

DETAILED DESCRIPTION OF THE INVENTION

The present invention is susceptible of embodiments in many different forms. Preferred embodiments of the invention are disclosed with the understanding that the present disclosure is to be considered as exemplifications of the principles of the invention and are not intended to limit the broad aspects of the invention to the embodiments illustrated.

The present invention provides a method for of treatment involving the ex-vivo delivery of pharmaceutical agents to a cell set followed by reinfusion of the now-treated cells to the host. This process can be autologous (same donor and recipient) or heterologous (different donor and recipient). The method generally involves: (1) the collection of tissue cells from a animal donor, (2) selective or non-selective growth of these cells in a cell culture medium to which is added a pharmaceutical composition comprising solid particles of a therapeutically active compound, preferably substantially carrier-free (defined below), with the purpose of either uptake of the active compound into the intracellular compartment of the cultured cells, attachment of the active compound to the periphery of such cells, or a combination of intracellular uptake and attachment to the cell surface, (3) optionally, isolation and/or resuspension of the cells prepared in steps 1 and 2, and (4) administration of the cellular suspension prepared in steps 1 through 3 to an animal. The following description of the pharmaceutical composition applies to all embodiments of this invention. The pharmaceutical composition can be poorly water soluble or water soluble. The pharmaceutical composition can also be a therapeutic agent or a diagnostic agent. The pharmaceutical composition can also be one or more compounds of similar or different therapeutic class. The therapeutic agents can include any compounds that are used to treat diseases in which affected tissues can be reached by administered cells that are loaded with a solid particulate form of the compound. Such diseases include, but are not limited to, bacterial, viral, and fungal infections, neoplasms, lysosomal storage disorders, inflammatory and autoimmune disorders, and metabolic disorders. Inflammatory and autoimmune disorders may include, but are not limited to, osteoarthritis, rheumatoid arthritis, Crohn's disease, cystitis, ileitis, colitis, lupus, multiple sclerosis, and amyotrophic lateral sclerosis.

"Substantially carrier-free" refers to a solid particle consisting of substantially pure pharmaceutical agent (about 90% or greater than 90% by weight), with surfactants or other excipients added to the suspension to either prevent aggregation or modulate release of the pharmaceutical agent from the solid particle. The suspension can be prepared by any of the methods described herein. The active agent particles will have an average effective diameter of less than about 100 microns and the liquid phase contains ingredients non-lethal to cells when added to a cell culture medium.

The pharmaceutical composition can further include a surfactant, alone or in combination with other surfactants, to stabilize the pharmaceutical composition. The surfactant can be selected from a variety of known anionic surfactants, cationic surfactants, zwitterionic surfactants, nonionic surfactants and surface active biological modifiers.

Therapeutic agents can be selected from a variety of known pharmaceuticals such as, but are not limited to: analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, anorexiants, antacids, antidiarrheals, antidotes, antifolics, antipyretics, antirheumatic agents, psychotherapeutic agents, neural blocking agents, anti-inflammatory agents, antihelmintics, antibiotics, anticoagulants, antidepressants, antiepileptics, antifungals, antihistamines, antimuscarinic agents, antimycobacterial agents, antineoplastic agents, antiprotozoal agents, antiviral agents, anxiolytic sedatives, beta-adrenoceptor blocking agents, contrast media, corticosteroids, cough suppressants, diagnostic agents, diagnostic imaging agents, dopaminergics, hemostatics, hematological agents, hypnotics, immuriological agents, muscarinics, parasympathomimetics, prostaglandins, protease inhibitors, radio-pharmaceuticals, sedatives, stimulants, sympathomimetics, vitamins, xanthines, growth factors, hormones, and antiprion agents. Antineoplastic agents can include paclitaxel and its derivative compounds, alkaloids, antimetabolites, enzyme inhibitors, alkylating agents and antibiotics. Other therapeutic agents include carbamazepine, prednisolone, and nabumetone.

Therapeutic agents can also include a biologic. The biologic can be selected from proteins, polypeptides, carbohydrates, polynucleotides, and nucleic acids. Nucleic acids include, but are not limited to, single or double stranded DNA, RNA generally and cDNA, t-RNA, mRNA, si-RNA and the like. The protein can be an antibody selected from polyclonal antibodies and monoclonal antibodies.

Diagnostic agents include the x-ray imaging agents and contrast media. Examples of x-ray imaging agents include WIN-8883 (ethyl 3,5-diacetamido-2,4,6-triiodobenzoate) also known as the ethyl ester of diatrazoic acid (EEDA), WIN 67722, i.e., (6-ethoxy-6-oxohexyl-3,5-bis(acetamido)-2,4,6-triiodobenzoate; ethyl-2-(3,5-bis(acetamido)-2,4,6-triiodobenzoyloxy) butyrate (WIN 16318); ethyl diatrizoxyacetate (WIN 12901); ethyl 2-(3,5-bis(acetamido)-2,4,6-triiodobenzoyloxy)propionate (WIN 16923); N-ethyl 2-(3,5-bis(acetamido)-2,4,6-triiodobenzoyloxy acetamide (WIN 65312); isopropyl 2-(3,5-bis(acetamido)-2,4,6-triiodobenzoyloxy) acetamide (WIN 12855); diethyl 2-(3,5-bis(acetamido)-2,4,6-triiodobenzoyloxy malonate (WIN 67721); ethyl 2-(3,5-bis(acetamido)-2,4,6-triiodobenzoyloxy) phenylacetate (WIN 67585); propanedioic acid, [[3,5-bis(acetylamino)-2,4,5-triodobenzoyl]oxy]bis(1-methyl)ester (WIN 68165); and benzoic acid, 3,5-bis(acetylamino)-2,4,6-triodo-4-(ethyl-3-ethoxy-2-butenoate) ester (WIN 68209). Preferred contrast agents include those that are expected to disintegrate relatively rapidly under physiological conditions, thus minimizing any particle associated inflammatory response. Disintegration may result from enzymatic hydrolysis, solubilization of carboxylic acids at physiological pH, or other mechanisms. Thus, poorly soluble iodinated carboxylic acids such as iodipamide, diatrizoic acid, and metrizoic acid, along with hydrolytically labile iodinated species such as WIN 67721, WIN 12901, WIN 68165, and WIN 68209 or others may be preferred.

Other contrast media include, but are not limited to, particulate preparations of magnetic resonance imaging aids such as gadolinium chelates, iron oxides, or other paramagnetic contrast agents. Examples of such compounds are gadopentetate dimeglumine (Magnevist®) and gadoteridol (Prohance®).

A description of classes of therapeutic agents and diagnostic agents and a listing of species within each class can be found in Martindale, The Extra Pharmacopoeia, Twenty-ninth Edition, The Pharmaceutical Press, London, 1989 which is incorporated herein by reference and made a part hereof. The therapeutic agents and diagnostic agents are commercially available and/or can be prepared by techniques known in the art.

Preferably the pharmaceutical composition is a poorly water-soluble compound. What is meant by "poorly water soluble" is a solubility of the compound in water of less than about 10 mg/mL, and preferably less than 1 mg/mL. These poorly water-soluble compounds are most suitable for aqueous suspension preparations since there are limited alternatives of formulating these compounds in an aqueous medium.

The following description of particles also applies to all embodiments of the present invention. The particles in the dispersion can be amorphous, semicrystalline, crystalline, or a combination thereof as determined by suitable analytical methods such as differential scanning calorimetry (DSC) or X-ray diffraction. Prior to administration, the pharmaceutical composition can be homogenized through a homogenization process. The pharmaceutical composition can also be homogenized through a microprecipitation/homogenization process, microprecipitation, or ultrasonication as well.

The dispersion of the pharmaceutical composition can be sterilized prior to administering. Sterilization can be performed by any medical sterilization process including heat sterilization or sterilization by gamma irradiation. It can also be sterilized by filtration, either directly as a dispersion having particle sizes under 200 nm, or by sterile filtration of the solutions used in the precipitation process, prior to forming the solid dispersion. Sterilization can also be accomplished by brief application of very high pressure (greater than 2000 atmospheres), or by a combination of high pressure and elevated temperature.

The present invention can be practiced with water-soluble compounds. These water soluble active compounds are mixed with a polymer (for example, polylactate-polyglycolate copolymer (PLGA), polycyanoacrylate, albumin, starch), or encapsulated in a surrounding vesicle that is impermeable to the pharmaceutical compound. This encapsulating vesicle can be a polymeric coating such as polyacrylate. Further, the small particles prepared from these water soluble compounds can be modified to improve chemical stability and control the pharmacokinetic properties of the compounds by controlling the release of the compounds from the particles. Examples of water-soluble compounds include, but are not limited to, simple organic compounds, proteins, peptides, nucleotides, oligonucleotides, and carbohydrates.

The particles utilized in the present invention have an average effective particle size of less than about 100 µm as measured by dynamic light scattering methods (e.g., photocorrelation spectroscopy, laser diffraction, low-angle laser light scattering (LALLS), medium-angle laser light scattering (MALLS)), light obscuration methods (Coulter method, for example), (HIAC) electrical resistance, rheology, or microscopy (light or electron). The preferred average effective particle size depends on factors such as the intended route of administration, formulation, solubility, toxicity and bioavailability of the compound.

A. Preparation of the Pharmaceutical Composition as Particles

The processes for preparing the particles used in the present invention can be accomplished through numerous techniques known to those skilled in the art. A representative, but non-exhaustive, discussion of techniques for preparing particle dispersions of pharmaceutical compositions follows.

I. Energy Addition Techniques for Forming Small Particle Dispersions

In general, the method of preparing small particle dispersions using energy addition techniques includes the step of adding the pharmaceutically active compound, which sometimes shall be referred to as a drug, in bulk form to a suitable vehicle such as water or aqueous solution containing one or more of the surfactants set forth below, or other liquid in which the pharmaceutical compound is not appreciably soluble, to form a first suspension, which shall be referred to as a presuspension. Energy is added to the presuspension to form a particle dispersion which is physically more stable than the presuspension. Alternatively, the energy addition step can be applied to dry powder form of the active compound. Energy is added by mechanical grinding (e.g., pearl milling, ball milling, hammer milling, fluid energy milling, jet milling, or wet grinding). Such techniques are disclosed in U.S. Pat. No. 5,145,684, which is incorporated herein by reference and made a part hereof.

Energy addition techniques further include subjecting the presuspension to high shear conditions including cavitation, shearing or impact forces utilizing a microfluidizer. The present invention further contemplates adding energy to the presuspension using a piston gap homogenizer or counter current flow homogenizer such as those disclosed in U.S. Pat. No. 5,091,188 which is incorporated herein by reference and made a part hereof. Suitable piston gap homogenizers are commercially available under the product name EMULSIFLEX by Avestin, and French Pressure Cells sold by Spectronic Instruments. Suitable microfluidizers are available from Microfluidics Corp.

The step of adding energy can also be accomplished using sonication techniques. The step of sonicating can be carried out with any suitable sonication device such as the Branson Model S-450A or Cole-Parmer 500/750 Watt Model. Such devices are well known in the industry. Typically the sonication device has a sonication horn or probe that is inserted into the presuspension to emit sonic energy into the solution. The sonicating device, in a preferred form of the invention, is operated at a frequency of from about 1 kHz to about 90 kHz and more preferably from about 20 kHz to about 40 kHz or any range or combination of ranges therein. The probe sizes can vary and preferably is in distinct sizes such as ½ inch or ¼ inch or the like.

Regardless of the energy addition technique used, the dispersion of small particles must be sterilized prior to use. Sterilization can be accomplished by heat sterilization, gamma irradiation, filtration (either directly as a dispersion having particle sizes under 200 nm, or by sterile filtration of the solutions used in the precipitation process, prior to forming the solid dispersion), and by application of very high pressure (greater than 2000 atmospheres), or by a combination of high pressure and elevated temperature.

II. Precipitation Methods for Preparing Submicron Sized Particle Dispersions

Small particle dispersions can also be prepared by precipitation techniques. The following is a description of examples of precipitation techniques.

Microprecipitation Methods

One example of a microprecipitation method is disclosed in U.S. Pat. No. 5,780,062, which is incorporated herein by reference and made a part hereof. The '062 patent discloses an organic compound precipitation process including: (i) dissolving the organic compound in a water-miscible first solvent; (ii) preparing a solution of polymer and an amphiphile in an aqueous second solvent and in which second solvent the organic compound is substantially insoluble whereby a polymer/amphiphile complex is formed; and (iii) mixing the solutions from steps (i) and (ii) so as to cause precipitation of an aggregate of the organic compound and the polymer/amphiphile complex.

Another example of a suitable precipitation process is disclosed in U.S. Pat. No. 6,607,784 and co-pending and commonly assigned U.S. Ser. Nos. 09/874,499; 09/874,637; and 10/021,692, which are incorporated herein by reference and made a part hereof. The processes disclosed include the steps of: (1) dissolving an organic compound in a water miscible first organic solvent to create a first solution; (2) mixing the first solution with a second solvent or water to precipitate the organic compound to create a presuspension; and (3) adding energy to the presuspension in the form of high-shear mixing or heat to provide a dispersion of small particles. Optionally, the first organic solvent is removed from the mixture by any suitable means such as centrifugation or filtration methods. Moreover, the continuous phase of the dispersion can be optionally replaced by another continuous phase by removing the first continuous phase using methods such as centrifugation and filtration, adding a second continuous phase and subsequently redispersing the solid material in the second continuous phase. One or more optional surface modifiers set forth below can be added to the first organic solvent or the second aqueous solution.

Emulsion Precipitation Methods

One suitable emulsion precipitation technique is disclosed in the co-pending and commonly assigned U.S. Ser. No. 09/964,273, which is incorporated herein by reference and is made a part hereof. In this approach, the process includes the steps of: (1) providing a multiphase system having an organic phase and an aqueous phase, the organic phase having a pharmaceutically active compound therein; and (2) sonicating the system to evaporate a portion of the organic phase to cause precipitation of the compound in the aqueous phase to form a dispersion of small particles. The step of providing a multiphase system includes the steps of: (1) mixing a water immiscible solvent with the pharmaceutically active compound to define an organic solution, (2) preparing an aqueous based solution with one or more surface active compounds, and (3) mixing the organic solution with the aqueous solution to form the multiphase system. The step of mixing the organic phase and the aqueous phase can include the use of piston gap homogenizers, colloidal mills, high speed stirring equipment, extrusion equipment, manual agitation or shaking equipment, microfluidizer, or other equipment or techniques for providing high shear conditions. The crude emulsion will have oil droplets in the water of a size of approximately less than 1 μm in diameter. The crude emulsion is sonicated to define a microemulsion and eventually to provide a dispersion of small particles.

Another approach to preparing a dispersion of small particles is disclosed in co-pending and commonly assigned U.S. Ser. No. 10/183,035, which is incorporated herein by reference and made a part hereof. The process includes the steps of: (1) providing a crude dispersion of a multiphase system having an organic phase and an aqueous phase, the organic phase having a pharmaceutical compound therein; (2) providing energy to the crude dispersion to form a fine dispersion; (3) freezing the fine dispersion; and (4) lyophilizing the fine dispersion to obtain small particles of the pharmaceutical compound. The small particles can be sterilized by the techniques set forth below or the small particles can be reconstituted in an aqueous medium and sterilized.

The step of providing a multiphase system includes the steps of: (1) mixing a water immiscible solvent with the pharmaceutically effective compound to define an organic solution; (2) preparing an aqueous based solution with one or more surface active compounds; and (3) mixing the organic solution with the aqueous solution to form the multiphase system. The step of mixing the organic phase and the aqueous phase includes the use of piston gap homogenizers, colloidal mills, high speed stirring equipment, extrusion equipment, manual agitation or shaking equipment, microfluidizer, or other equipment or techniques for providing high shear conditions.

Solvent-Antisolvent Precipitation

Small particle dispersions can also be prepared using solvent anti-solvent precipitation technique disclosed by Fessi et al. in U.S. Pat. No. 5,118,528 and by Leclef et al. in U.S. Pat. No. 5,100,591 which are incorporated herein by reference and made a part hereof. Both processes include the steps of: (1) preparing a liquid phase of a biologically active substance in a solvent or a mixture of solvents to which may be added one or more surfactants; (2) preparing a second liquid phase of a non-solvent or a mixture of non-solvents, the non-solvent is miscible with the solvent or mixture of solvents for the substance; (3) adding together the solutions of (1) and (2) with stirring; and (4) removing of unwanted solvents to produce a dispersion of small particles. These methods are distinguished from those described under the above section, "Microprecipitation Methods", in that they do not provide for a last step of adding energy to the suspension in the form of high-shear mixing or heat.

Phase Inversion Precipitation

Small particle dispersions can be formed using phase inversion precipitation as disclosed in U.S. Pat. Nos. 6,235,224, 6,143,211 and U.S. patent application Ser. No. 2001/0042932, each of which is incorporated herein by reference and made a part hereof. Phase inversion is a term used to describe the physical phenomena by which a polymer dissolved in a continuous phase solvent system inverts into a solid macromolecular network in which the polymer is the continuous phase. One method to induce phase inversion is by the addition of a nonsolvent to the continuous phase. The polymer undergoes a transition from a single phase to an unstable two phase mixture: polymer rich and polymer poor fractions. Micellar droplets of nonsolvent in the polymer rich phase serve as nucleation sites and become coated with polymer. The '224 patent discloses that phase inversion of polymer solutions under certain conditions can bring about spontaneous formation of discrete microparticles, including nanoparticles. The '224 patent discloses dissolving or dispersing a polymer in a solvent. A pharmaceutical agent is also dissolved or dispersed in the solvent. For the crystal seeding step to be effective in this process it is desirable the agent is dissolved in the solvent. The polymer, the agent and the solvent together form a mixture having a continuous phase, wherein the solvent is the continuous phase. The mixture is then introduced into at least tenfold excess of a miscible nonsolvent to cause the spontaneous formation of the microencapsulated microparticles of the agent having an average particle size of between 10 nm and 10 μm. The particle size is influenced by the solvent:nonsolvent volume ratio, polymer concentration, the viscosity of the polymer-solvent solution, the molecular weight of the polymer, and the characteristics of the solvent-nonsolvent pair.

pH Shift Precipitation

Small particle dispersions can be formed by pH shift precipitation techniques. Such techniques typically include a step of dissolving a drug in a solution having a pH where the drug is soluble, followed by the step of changing the pH to a point where the drug is no longer soluble. The pH can be acidic or basic, depending on the particular pharmaceutical compound. The solution is then neutralized to form a dispersion of small particles. One suitable pH shifting precipitation process is disclosed in U.S. Pat. No. 5,665,331, which is incorporated herein by reference and made a part hereof. The process includes the step of dissolving of the pharmaceutical agent together with a crystal growth modifier (CGM) in an alkaline solution and then neutralizing the solution with an acid in the presence of suitable surface-modifying surface-active agent or agents to form a small particle dispersion of the pharmaceutical agent. The precipitation step can be followed by steps of diafiltration clean-up of the dispersion and then adjusting the concentration of the dispersion to a desired level.

Other examples of pH shifting precipitation methods are disclosed in U.S. Pat. Nos. 5,716,642; 5,662,883; 5,560,932; and 4,608,278, which are incorporated herein by reference and are made a part hereof.

Infusion Precipitation Method

Suitable infusion precipitation techniques to form small particle dispersions are disclosed in the U.S. Pat. Nos. 4,997,454 and 4,826,689, which are incorporated herein by reference and made a part hereof. First, a suitable solid compound is dissolved in a suitable organic solvent to form a solvent mixture. Then, a precipitating nonsolvent miscible with the organic solvent is infused into the solvent mixture at a temperature between about −10° C. and about 100° C. and at an infusion rate of from about 0.01 ml per minute to about 1000 ml per minute per volume of 50 ml to produce a suspension of precipitated non-aggregated solid particles of the compound with a substantially uniform mean diameter of less than 10 μm. Agitation (e.g., by stirring) of the solution being infused with the precipitating nonsolvent is preferred. The nonsolvent may contain a surfactant to stabilize the particles against aggregation. The particles are then separated from the solvent. Depending on the solid compound and the desired particle size, the parameters of temperature, ratio of nonsolvent to solvent, infusion rate, stir rate, and volume can be varied according to the invention. The particle size is proportional to the ratio of nonsolvent:solvent volumes and the temperature of infusion and is inversely proportional to the infusion rate and the stirring rate. The precipitating nonsolvent may be aqueous or non-aqueous, depending upon the relative solubility of the compound and the desired suspending vehicle.

Temperature Shift Precipitation

Temperature shift precipitation techniques may also be used to form small particle dispersions. This technique is disclosed in U.S. Pat. No. 5,188,837, which is incorporated herein by reference and made a part hereof. In an embodiment of the invention, liposheres are prepared by the steps of: (1) melting or dissolving a substance such as a drug to be delivered in a molten vehicle to form a liquid of the substance to be delivered; (2) adding a phospholipid along with an aqueous medium to the melted substance or vehicle at a temperature higher than the melting temperature of the substance or vehicle; (3) mixing the suspension at a temperature above the melting temperature of the vehicle until a homogenous fine preparation is obtained; and then (4) rapidly cooling the preparation to room temperature or below.

Solvent Evaporation Precipitation

Solvent evaporation precipitation techniques are disclosed in U.S. Pat. No. 4,973,465 which is incorporated herein by reference and made a part hereof. The '465 patent discloses methods for preparing microcrystals including the steps of: (1) providing a solution of a pharmaceutical composition and a phospholipid dissolved in a common organic solvent or combination of solvents, (2) evaporating the solvent or solvents and (3) suspending the film obtained by evaporation of the solvent or solvents in an aqueous solution by vigorous stirring to form a dispersion of small particles. The solvent can be removed by evaporating a sufficient quantity of the solvent to cause precipitation of the compound. The solvent can also be removed by other well known techniques such as applying a vacuum to the solution or blowing nitrogen over the solution.

Reaction Precipitation

Reaction precipitation includes the steps of dissolving the pharmaceutical compound, and optionally other excipients, into a suitable solvent to form a solution. The compound may be added in an amount at or below the saturation point of the compound in the solvent. The compound or any of the excipients is precipitated from solution by reacting with a chemical agent or by modification in response to adding energy such as heat or UV light or the like such that the modified compound has a lower solubility in the solvent and precipitates from the solution to form a small particle dispersion. Precipitation of excipient provides a solid matrix into which the drug is sorbed.

Compressed Fluid Precipitation

A suitable technique for precipitating by compressed fluid is disclosed in WO 97/14407 to Johnston, which is incorporated herein by reference and made a part hereof. The method includes the steps of dissolving a water-insoluble drug in a solvent to form a solution. The solution is then sprayed into a compressed fluid, which can be a gas, liquid or supercritical fluid. The addition of the compressed fluid to a solution of a solute in a solvent causes the solute to attain or approach supersaturated state and to precipitate out as fine particles. In this case, the compressed fluid acts as an anti-solvent which lowers the cohesive energy density of the solvent in which the drug is dissolved.

Alternatively, the drug can be dissolved in the compressed fluid which is then sprayed into an aqueous phase. The rapid expansion of the compressed fluid reduces the solvent power of the fluid, which in turn causes the solute to precipitate out as small particles in the aqueous phase. In this case, the compressed fluid acts as a solvent.

In order to stabilize the particles against aggregation, a surface modifier, such as a surfactant, is included in this technique.

Spraying into Cryogenic Fluids

A suitable technique for precipitating by compressed fluid is disclosed by Williams et al. in U.S. application Ser. No. 10/273,730, which is incorporated herein by reference and made a part hereof. The method provides a system and method for the production of small particles wherein the active ingredient is mixed with water, one or more solvents, or a combination thereof, and the resulting mixture sprayed at or below the surface of a cryogenic fluid. Frozen particles are thereby provided. Materials for encapsulating the solid particles may also be added so that frozen particles are generated wherein the encapsulating agent surrounds the active agent.

Protein Microsphere Precipitation

Microspheres or microparticles utilized in this invention can also be produced from a process involving mixing or dissolving macromolecules such as proteins with a water soluble polymer. This process is disclosed in U.S. Pat. Nos. 5,849,884, 5,981,719, 6,090,925, 6,268,053, 6,458,387, and U.S. patent application Ser. No. 10/399,829, which are incorporated herein by reference and made a part hereof. In an embodiment of the invention, microspheres are prepared by mixing a macromolecule in solution with a polymer or a mixture of polymers in solution at a pH near the isoelectric point of the macromolecule. The mixture is incubated in the presence of an energy source, such as heat, radiation, or ionization, or, alternatively, by removing energy, e.g., cooling, for a predetermined amount of time. The resulting microspheres can be removed from any unincorporated components present in the solution by physical separation methods.

There are numerous other methodologies for preparing small particle dispersions. The present invention provides a methodology for terminally sterilizing such dispersions without significantly impacting the efficacy of the preparation.

III. Additional Methods for Preparing Particle Dispersions of Pharmaceutical Compositions The following additional processes for preparing particles of pharmaceutical compositions (i.e. organic compound) used in the present invention can be separated into four general categories. Each of the categories of processes share the steps of: (1) dissolving an organic compound in a water miscible first solvent to create a first solution, (2) mixing the first solution with a second solvent of water to precipitate the organic compound to create a pre-suspension, and (3) adding energy to the presuspension in the form of high-shear mixing or heat, or a combination of both, to provide a stable form of the organic compound having the desired size ranges defined above. The mixing steps and the adding energy step can be carried out in consecutive steps or simultaneously.

The categories of processes are distinguished based upon the physical properties of the organic compound as determined through x-ray diffraction studies, DSC studies, or other suitable study conducted prior to the energy-addition step and after the energy-addition step. In the first process category, prior to the energy-addition step the organic compound in the presuspension takes an amorphous form, a semi-crystalline form or a supercooled liquid form and has an average effective particle size. After the energy-addition step the organic compound is in a crystalline form having an average effective particle size essentially the same or less than that of the presuspension.

In the second process category, prior to the energy-addition step the organic compound is in a crystalline form and has an average effective particle size. After the energy-addition step the organic compound is in a crystalline form having essentially the same average effective particle size as prior to the energy-addition step but the crystals after the energy-addition step are less likely to aggregate or form large crystals.

The lower tendency of the organic compound to aggregate or form large crystals is observed by laser dynamic light scattering and light microscopy.

In the third process category, prior to the energy-addition step the organic compound is in a crystalline form that is friable and has an average effective particle size. What is meant by the term "friable" is that the particles are fragile and are more easily broken down into smaller particles. After the energy-addition step the organic compound is in a crystalline form having an average effective particle size smaller than the crystals of the pre-suspension. By taking the steps necessary to place the organic compound in a crystalline form that is friable, the subsequent energy-addition step can be carried out more quickly and efficiently when compared to an organic compound in a less friable crystalline morphology.

In the fourth process category, the first solution and second solvent are simultaneously subjected to the energy-addition step. Thus, the physical properties of the organic compound before and after the energy addition step were not measured.

The energy-addition step can be carried out in any fashion wherein the presuspension or the first solution and second solvent are exposed to cavitation, shearing or impact forces. In one preferred form, the energy-addition step is an annealing step. Annealing is defined in this invention as the process of converting matter that is thermodynamically unstable into a more stable form by single or repeated application of energy (direct heat or mechanical stress), followed by thermal relaxation. This lowering of energy may be achieved by conversion of the solid form from a less ordered to a more ordered lattice structure. Alternatively, this stabilization may occur by a reordering of the surfactant molecules at the solid-liquid interface.

These four process categories are shown separately below. It should be understood, however, that the process conditions such as choice of surfactants or combination of surfactants, amount of surfactant used, temperature of reaction, rate of mixing of solutions, rate of precipitation and the like can be selected to allow for any drug to be processed under any one of the categories discussed next.

The first process category, as well as the second, third, and fourth process categories, can be further divided into two subcategories, Method A and B.

The first solvent according to the following processes is a solvent or mixture of solvents in which the organic compound of interest is relatively soluble and which is miscible with the second solvent. Such solvents include, but are not limited to water-miscible protic compounds, in which a hydrogen atom in the molecule is bound to an electronegative atom such as oxygen, nitrogen, or other Group VA, VIA and VII A in the Periodic Table of elements. Examples of such solvents include, but are not limited to, alcohols, amines (primary or secondary), oximes, hydroxamic acids, carboxylic acids, sulfonic acids, phosphonic acids, phosphoric acids, amides and ureas.

Other examples of the first solvent also include aprotic organic solvents. Some of these aprotic solvents can form hydrogen bonds with water, but can only act as proton acceptors because they lack effective proton donating groups. One class of aprotic solvents is a dipolar aprotic solvent, as defined by the International Union of Pure and Applied Chemistry (IUPAC Compendium of Chemical Terminology, 2nd Ed., 1997):

A solvent with a comparatively high relative permittivity (or dielectric constant), greater than ca. 15, and a sizable permanent dipole moment, that cannot donate suitably labile hydrogen atoms to form strong hydrogen bonds, e.g. dimethyl sulfoxide.

Dipolar aprotic solvents can be selected from the group consisting of: amides (fully substituted, with nitrogen lacking attached hydrogen atoms), ureas (fully substituted, with no hydrogen atoms attached to nitrogen), ethers, cyclic ethers, nitriles, ketones, sulfones, sulfoxides, fully substituted phosphates, phosphonate esters, phosphoramides, nitro compounds, and the like. Dimethylsulfoxide (DMSO), N-methyl-2-pyrrolidinone (NMP), 2-pyrrolidinone, 1,3-dimethylimidazolidinone (DMI), dimethylacetamide (DMA), dimethylformamide (DMF), dioxane, acetone, tetrahydrofuran (THF), tetramethylenesulfone (sulfolane), acetonitrile, and hexamethylphosphoramide (HMPA), nitromethane, among others, are members of this class.

Solvents may also be chosen that are generally water-immiscible, but have sufficient water solubility at low volumes (less than 10%) to act as a water-miscible first solvent at these reduced volumes. Examples include aromatic hydrocarbons, alkenes, alkanes, and halogenated aromatics, halogenated alkenes and halogenated alkanes. Aromatics include, but are not limited to, benzene (substituted or unsubstituted), and monocyclic or polycyclic arenes. Examples of substituted benzenes include, but are not limited to, xylenes (ortho, meta, or para), and toluene. Examples of alkanes include but are not limited to hexane, neopentane, heptane, isooctane, and cyclohexane. Examples of halogenated aromatics include, but are not restricted to, chlorobenzene, bromobenzene, and chlorotoluene. Examples of halogenated alkanes and alkenes include, but are not restricted to, trichloroethane, methylene chloride, ethylenedichloride (EDC), and the like.

Examples of the all of the above solvent classes include but are not limited to: N-methyl-2-pyrrolidinone (also called N-methyl-2-pyrrolidone), 2-pyrrolidinone (also called 2-pyrrolidone), 1,3-dimethyl-2-imidazolidinone (DMI), dimethylsulfoxide, dimethylacetamide, acetic acid, lactic acid, methanol, ethanol, isopropanol, 3-pentanol, n-propanol, benzyl alcohol, glycerol, butylene glycol (butanediol), ethylene glycol, propylene glycol, mono- and diacylated monoglycerides (such as glyceryl caprylate), dimethyl isosorbide, acetone, dimethylsulfone, dimethylformamide, 1,4-dioxane, tetramethylenesulfone (sulfolane), acetonitrile, nitromethane, tetramethylurea, hexamethylphosphoramide (HMPA), tetrahydrofuran (THF), dioxane, diethylether, tert-butylmethyl ether (TBME), aromatic hydrocarbons, alkenes, alkanes, halogenated aromatics, halogenated alkenes, halogenated alkanes, xylene, toluene, benzene, substituted benzene, ethyl acetate, methyl acetate, butyl acetate, chlorobenzene, bromobenzene, chlorotoluene, trichloroethane, methylene chloride, ethylenedichloride (EDC), hexane, neopentane, heptane, isooctane, cyclohexane, polyethylene glycol (PEG, for example, PEG-4, PEG-8, PEG-9, PEG-12, PEG-14, PEG-16, PEG-120, PEG-75, PEG-150), polyethylene glycol esters (examples such as PEG-4 dilaurate, PEG-20 dilaurate, PEG-6 isostearate, PEG-8 palmitostearate, PEG-150 palmitostearate), polyethylene glycol sorbitans (such as PEG-20 sorbitan isostearate), polyethylene glycol monoalkyl ethers (examples such as PEG-3 dimethyl ether, PEG-4 dimethyl ether), polypropylene glycol (PPG), polypropylene alginate, PPG-10 butanediol, PPG-10 methyl glucose ether, PPG-20 methyl glucose ether, PPG-15 stearyl ether, propylene glycol dicaprylate/dicaprate, propylene glycol laurate, and glycofurol (tetrahydrofurfuryl alcohol polyethylene glycol ether). A preferred first solvent is N-methyl-2-pyrrolidinone. Another preferred first solvent is lactic acid.

The second solvent is an aqueous solvent. This aqueous solvent may be water by itself. This solvent may also contain buffers, salts, surfactant(s), water-soluble polymers, and combinations of these excipients.

Method A

In Method A (see FIG. 1), the organic compound ("drug") is first dissolved in the first solvent to create a first solution. The organic compound can be added from about 0.1% (w/v) to about 50% (w/v) depending on the solubility of the organic compound in the first solvent. Heating of the concentrate from about 30° C. to about 100° C. may be necessary to ensure total dissolution of the compound in the first solvent.

A second aqueous solvent is provided with one or more optional surface modifiers such as an anionic surfactant, a cationic surfactant, a zwitterionic surfactant, a nonionic surfactant or a biologically surface active molecule added thereto. Suitable anionic surfactants include but are not limited to alkyl sulfonates, alkyl phosphates, alkyl phosphonates, potassium laurate, triethanolamine stearate, sodium lauryl sulfate, sodium dodecylsulfate, alkyl polyoxyethylene sulfates, sodium alginate, dioctyl sodium sulfosuccinate, phosphatidyl glycerol, phosphatidyl inosine, phosphatidylinositol, diphosphatidylglycerol, phosphatidylserine, phosphatidic acid and their salts, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate, etc.).

Zwitterionic surfactants are electrically neutral but possess local positive and negative charges within the same molecule. Suitable zwitterionic surfactants include but are not limited to zwitterionic phospholipids. Suitable phospholipids include phosphatidylcholine, phosphatidylethanolamine, diacylglycero-phosphoethanolamine (such as dimyristoyl-glycero-phosphoethanolamine (DMPE), dipahnitoyl-glycero-phosphoethanolamine (DPPE), distearoyl-glycero-phosphoethanolamine (DSPE), and dioleolyl-glycero-phosphoethanolamine (DOPE)). Mixtures of phospholipids that include anionic and zwitterionic phospholipids may be employed in this invention. Such mixtures include but are not limited to lysophospholipids, egg or soybean phospholipid or any combination thereof. The phospholipid, whether anionic, zwitterionic or a mixture of phospholipids, may be salted or desalted, hydrogenated or partially hydrogenated or natural semisynthetic or synthetic. The phospholipid may also be conjugated with a water-soluble or hydrophilic polymer to specifically target the delivery to macrophages in the present invention. However, conjugated phospholipids may be used to target other cells or tissue in other applications. A preferred polymer is polyethylene glycol (PEG), which is also known as the monomethoxy polyethyleneglycol (mPEG). The molecule weights of the PEG can vary, for example, from 200 to 50,000. Some commonly used PEG's that are commercially available include PEG 350, PEG 550, PEG 750, PEG 1000, PEG 2000, PEG 3000, and PEG 5000. The phospholipid or the PEG-phospholipid conjugate may also incorporate a functional group which can covalently attach to a ligand including but not limited to proteins, peptides, carbohydrates, glycoproteins, antibodies, or pharmaceutically active agents. These functional groups may conjugate with the ligands through, for example, amide bond formation, disulfide or thioether formation, or biotin/streptavidin binding. Examples of the ligand-binding functional groups include but are not limited to hexanoylamine, dodecanylamine, 1,12-dodecanedicarboxylate, thioethanol, 4-(p-maleimidophenyl)butyramide (MPB), 4-(p-maleimidomethyl)cyclohexane-carboxamide (MCC), 3-(2-pyridyldithio)propionate (PDP), succinate, glutarate, dodecanoate, and biotin.

Suitable cationic surfactants include but are not limited to quaternary ammonium compounds, such as benzalkonium chloride, cetyltrimethylammonium bromide, chitosans, lauryldimethylbenzylammonium chloride, acyl carnitine hydrochlorides, dimethyldioctadecylammomium bromide (DDAB), dioleyoltrimethylammonium propane (DOTAP), dimyristoyltrimethylammonium propane (DMTAP), dimethylaminoethanecarbamoyl cholesterol (DC-Chol), 1,2-diacylglycero-3-(O-alkyl)phosphocholine, O-alkylphosphatidylcholine, alkyl pyridinium halides, or long-chain alkyl amines such as, for example, n-octylamine and oleylamine.

Suitable nonionic surfactants include: glyceryl esters, polyoxyethylene fatty alcohol ethers (Macrogol and Brij), polyoxyethylene sorbitan fatty acid esters (Polysorbates), polyoxyethylene fatty acid esters (Myrj), sorbitan esters (Span), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxamers), poloxamines, methylcellulose, hydroxymethylcellulose, hydroxypropylcellulose, hydroxypropylmethylcellulose, noncrystalline cellulose, polysaccharides including starch and starch derivatives such as hydroxyethylstarch (HES), polyvinyl alcohol, and polyvinylpyrrolidone. In a preferred form, the nonionic surfactant is a polyoxyethylene and polyoxypropylene copolymer and preferably a block copolymer of propylene glycol and ethylene glycol. Such polymers are sold under the tradename POLOXAMER also sometimes referred to as PLURONIC®, and sold by several suppliers including Spectrum Chemical and Ruger. Among polyoxyethylene fatty acid esters is included those having short alkyl chains. One example of such a surfactant is SOLUTOL® HS 15, polyethylene-660-hydroxystearate, manufactured by BASF Aktiengesellschaft. Surface-active biological molecules include such molecules as albumin, casein, hirudin or other appropriate proteins. Polysaccharide biologics are also included, and consist of but are not limited to, starches, heparins, and chitosans. Other suitable surfactants include any amino acids such as leucine, alanine, valine, isoleucine, lysine, aspartic acid, glutamic acid, methionine, phenylalanine, or any derivatives of these amino acids such as, for example, amide or ester derivatives and polypeptides formed from these amino acids.

It may also be desirable to add a pH adjusting agent to the second solvent. Suitable pH adjusting agents include, but are not limited to, hydrochloric acid, sulftric acid, phosphoric acid, monocarboxylic acids (such as, for example, acetic acid and lactic acid), dicarboxylic acids (such as, for example, succinic acid), tricarboxylic acids (such as, for example, citric acid), THAM (tris(hydroxymethyl)aminomethane), meglumine (N-methylglucosamine), sodium hydroxide, and amino acids such as glycine, arginine, lysine, alanine, histidine and leucine. The second solvent should have a pH within the range of from about 3 to about 11. The aqueous medium may additionally include an osmotic pressure adjusting agent, such as but not limited to glycerin, a monosaccharide such as dextrose, a disaccharide such as sucrose, a trisaccharide such as raffinose, and sugar alcohols such as mannitol, xylitol and sorbitol.

In a preferred form, the method for preparing small particles of an organic compound includes the steps of adding the first solution to the second solvent. The addition rate is dependent on the batch size, and precipitation kinetics for the organic compound. Typically, for a small-scale laboratory process (preparation of 1 liter), the addition rate is from about 0.05 cc per minute to about 10 cc per minute. During the addition, the solutions should be under constant agitation. It has been observed using light microscopy that amorphous particles, semi-crystalline solids, or a supercooled liquid are formed to create a pre-suspension. The method further includes the step of subjecting the pre-suspension to an energy-addition step to convert the amorphous particles, supercooled liquid or semicrystalline solid to a more stable, crystalline solid state. The resulting particles will have an average effective particles size as measured by dynamic light scattering methods. In process category four, the first solution and the second solvent are combined while simultaneously conducting the energy-addition step.

The energy-addition step involves adding energy through sonication, homogenization, countercurrent flow homogenization, microfluidization, or other methods of providing impact, shear or cavitation forces. The sample may be cooled or heated during this stage. In one preferred form, the energy-addition step is effected by a piston gap homogenizer such as the one sold by Avestin Inc. under the product designation EmulsiFlex-C160. In another preferred form, the energy-addition step may be accomplished by ultrasonication using an ultrasonic processor such as the Vibra-Cell Ultrasonic Processor (600 W), manufactured by Sonics and Materials, Inc. In yet another preferred form, the energy-addition step may be accomplished by use of an emulsification apparatus as described in U.S. Pat. No. 5,720,551 which is incorporated herein by reference and made a part hereof.

Depending upon the rate of energy addition, it may be desirable to adjust the temperature of the processed sample to within the range of from approximately −30° C. to 30° C. Alternatively, in order to effect a desired phase change in the processed solid, it may also be necessary to heat the pre-suspension to a temperature within the range of from about 30° C. to about 100° C. during the energy-addition step.

Method B

Method B differs from Method A in the following respects. The first difference is a surfactant or combination of surfactants is added to the first solution. The surfactants may be selected from the groups of anionic, nonionic, cationic surfactants, and surface-active biological modifiers set forth above.

A drug suspension resulting from application of the processes may be administered directly as an injectable solution, provided Water for Injection is used in formulation and an appropriate means for solution sterilization is applied. Sterilization may be accomplished by methods well known in the art such as steam or heat sterilization, gamma irradiation and the like. Other sterilization methods, especially for particles in which greater than 99% of the particles are less than 200 nm, would also include pre-filtration first through a 3.0 micron filter followed by filtration through a 0.45-micron particle filter, followed by steam or heat sterilization or sterile filtration through two redundant 0.2-micron membrane filters. Yet another means of sterilization is sterile filtration of the concentrate prepared from the first solvent containing drug and optional surfactant or surfactants and sterile filtration of the aqueous diluent. These are then combined in a sterile mixing container, preferably in an isolated, sterile environment. Mixing, homogenization, and further processing of the suspension are then carried out under aseptic conditions.

Yet another procedure for sterilization would consist of heat sterilization or autoclaving within the homogenizer itself, before, during, or subsequent to the homogenization step. Processing after this heat treatment would be carried out under aseptic conditions.

Optionally, a solvent-free suspension may be produced by solvent removal after precipitation. This can be accomplished by centrifugation, dialysis, diafiltration, force-field fractionation, high-pressure filtration, reverse osmosis, or other separation techniques well known in the art. Complete removal of N-methyl-2-pyrrolidinone was typically carried out by one to three successive centrifugation runs; after each centrifugation (18,000 rpm for 30 minutes) the supernatant was decanted and discarded. A fresh volume of the suspension vehicle without the organic solvent was added to the remaining solids and the mixture was dispersed by homogenization. It will be recognized by those skilled in the art that other high-shear mixing techniques could be applied in this reconstitution step. Alternatively, the solvent-free particles can be formulated into various dosage forms as desired for a variety of administrative routes, such as oral, pulmonary, nasal, topical, intramuscular, and the like.

Furthermore, any undesired excipients such as surfactants may be replaced by a more desirable excipient by use of the separation methods described in the above paragraph. The solvent and first excipient may be discarded with the supernatant after centrifugation or filtration. A fresh volume of the suspension vehicle without the solvent and without the first excipient may then be added. Alternatively, a new surfactant may be added. For example, a suspension consisting of drug, N-methyl-2-pyrrolidinone (solvent), poloxamer 188 (first excipient), sodium deoxycholate, glycerol and water may be replaced with phospholipids (new surfactant), glycerol and water after centrifugation and removal of the supernatant.

I. First Process Category

The methods of the first process category generally include the step of dissolving the organic compound in a water miscible first solvent followed by the step of mixing this solution with an aqueous solvent to form a presuspension wherein the organic compound is in an amorphous form, a semicrystalline form or in a supercooled liquid form as determined by x-ray diffraction studies, DSC, light microscopy or other analytical techniques and has an average effective particle size within one of the effective particle size ranges set forth above. The mixing step is followed by an energy-addition step.

II. Second Process Category

The methods of the second processes category include essentially the same steps as in the steps of the first processes category but differ in the following respect. An x-ray diffraction, DSC or other suitable analytical techniques of the pre-suspension shows the organic compound in a crystalline form and having an average effective particle size. The organic compound after the energy-addition step has essentially the same average effective particle size as prior to the energy-addition step but has less of a tendency to aggregate into larger particles when compared to that of the particles of the presuspension. Without being bound to a theory, it is believed the differences in the particle stability may be due to a reordering of the surfactant molecules at the solid-liquid interface.

III. Third Process Category

The methods of the third category modify the first two steps of those of the first and second processes categories to ensure the organic compound in the presuspension is in a friable form having an average effective particle size (e.g., such as slender needles and thin plates). Friable particles can be formed by selecting suitable solvents, surfactants or combination of surfactants, the temperature of the individual solutions, the rate of mixing and rate of precipitation and the like. Friability may also be enhanced by the introduction of lattice defects (e.g., cleavage planes) during the steps of mixing the first solution with the aqueous solvent. This would arise by rapid crystallization such as that afforded in the precipitation step. In the energy-addition step these friable crystals are converted to crystals that are kinetically stabilized and having an average effective particle size smaller than those of the presuspension. Kinetically stabilized means particles have a reduced tendency to aggregate when compared to particles that are not kinetically stabilized. In such instance the energy-addition step results in a breaking up of the friable particles. By ensuring the particles of the presuspension are in a friable state, the organic compound can more easily and more quickly be prepared into a particle within the desired size ranges when compared to processing an organic compound where the steps have not been taken to render it in a friable form.

IV. Fourth Process Category

The methods of the fourth process category include the steps of the first process category except that the mixing step is carried out simultaneously with the energy-addition step.

Polymorph Control

The present process further provides additional steps for controlling the crystal structure of an organic compound to ultimately produce a suspension of the compound in the desired size range and a desired crystal structure. What is meant by the term "crystal structure" is the arrangement of the atoms within the unit cell of the crystal. Compounds that can be crystallized into different crystal structures are said to be polymorphic. Identification of polymorphs is important step in drug formulation since different polymorphs of the same drug can show differences in solubility, therapeutic activity, bioavailability, and suspension stability. Accordingly, it is important to control the polymorphic form of the compound for ensuring product purity and batch-to-batch reproducibility.

The steps to control the polymorphic form of the compound includes seeding the first solution, the second solvent or the pre-suspension to ensure the formation of the desired polymorph. Seeding includes using a seed compound or adding energy. In a preferred form the seed compound is a pharmaceutically-active compound in the desired polymorphic form. Alternatively, the seed compound can also be an inert impurity, a compound unrelated in structure to the desired polymorph but with features that may lead to templating of a crystal nucleus, or an organic compound with a structure similar to that of the desired polymorph.

The seed compound can be precipitated from the first solution. This method includes the steps of adding the organic compound in sufficient quantity to exceed the solubility of the organic compound in the first solvent to create a supersaturated solution. The supersaturated solution is treated to precipitate the organic compound in the desired polymorphic form. Treating the supersaturated solution includes aging the solution for a time period until the formation of a crystal or crystals is observed to create a seeding mixture. It is also possible to add energy to the supersaturated solution to cause the organic compound to precipitate out of the solution in the desired polymorph. The energy can be added in a variety of ways including the energy addition steps described above. Further energy can be added by heating, or by exposing the pre-suspension to electromagnetic energy, particle beam or electron beam sources. The electromagnetic energy includes light energy (ultraviolet, visible, or infrared) or coherent radiation such as that provided by a laser, microwave energy such as that provided by a maser (microwave amplification by stimulated emission of radiation), dynamic electromagnetic energy, or other radiation sources. It is further contemplated utilizing ultrasound, a static electric field, or a static magnetic field, or combinations of these, as the energy-addition source.

In a preferred form, the method for producing seed crystals from an aged supersaturated solution includes the steps of: (i) adding a quantity of an organic compound to the first organic solvent to create a supersaturated solution, (ii) aging the supersaturated solution to form detectable crystals to create a seeding mixture; and (iii) mixing the seeding mixture with the second solvent to precipitate the organic compound to create a pre-suspension. The presuspension can then be further processed as described in detail above to provide an aqueous suspension of the organic compound in the desired polymorph and in the desired size range.

Seeding can also be accomplished by adding energy to the first solution, the second solvent or the pre-suspension provided that the exposed liquid or liquids contain the organic compound or a seed material. The energy can be added in the same fashion as described above for the supersaturated solution.

Accordingly, the present processes utilize a composition of matter of an organic compound in a desired polymorphic form essentially free of the unspecified polymorph or polymorphs. In a preferred form, the organic compound is a pharmaceutically active substance. It is contemplated the methods described herein can be used to selectively produce a desired polymorph for numerous pharmaceutically active compounds.

B. Ex-Vivo Delivery of Solid Drug Particulate

There are numerous types of cells in the mammalian subject that are capable of phagocytosis and transport of particles. These cells include, but are not limited to, macrophages, monocytes, granulocytes, neutrophils, basophils, eosinophils and dendritic cells Particles in the size range of from about 150 nm to about 100 microns are more readily taken up by these phagocytic organisms. Particles smaller than 150 nm may also associate in-vitro and ex-vivo with cells by attachment to or association with the cell surface. They may be subsequently taken into the cells by pinocytosis, which is an invagination of the cell membrane to form an intracellular capsule around the particle. In pinocytosis ("cell drinking"), the engulfed particle is relatively small (e.g., 20 nm) (Watts, C; Marsh, M. Endocytosis: what goes in and how? J Cell Sci. 1992; 103(1):1-8). Pinocytosis occurs continuously in almost all eucaryotic cells.

Isolating macrophages from the mammalian subject can be performed by a cell separator. For instance, the Isolex cell separator (Baxter Healthcare Corp., Deerfield, Ill.) can be used to isolate various cells. Other methods, known to those skilled in the art of ex-vivo cell isolation could be employed to obtain cells useful in the present invention methods. Such methods include, but are not limited to, pheresis of peripheral blood; by mobilization of bone marrow cells through G-CSF or GM-CSF, e.g., or by direct removal of marrow cells by spinal, sternal, lumbar, or iliac crest puncture.

Once isolated, the cells are nurtured in a selective or non-selective growth medium and simultaneously or later contacted with the particulate pharmaceutical composition and incubated for short period of time to allow for cell uptake or adsorption of the particles.

The concentrations of pharmaceutical composition used in the ex-vivo procedure will vary due to several factors, including, but not limited to, type of cells used, concentration of cells, pharmaceutical agent employed, size of the small particle dispersions, disease to be treated, and so on. Generally, however, the cellular isolates will be contacted with about 1 to about 300 mg/ml of a pharmaceutical composition of the present invention.

The cells can be incubated with the pharmaceutical composition for up to 24 hours or longer to permit sufficient cell uptake of the drug particles. Uptake by the cells of the dispersion of the pharmaceutical composition as particles may include phagocytosis, or other means of endocytosis, or adsorption of the particle onto the surface of the cells. Furthermore, in a preferred form of the invention, the particles during contact with the cells are at a concentration higher than the thermodynamic saturation solubility thereby allowing the particles to remain in particulate form during uptake and delivery to the mammalian subject.

For marginally soluble drugs, the ex-vivo procedure can be utilized provided that the isolated cells are able to engulf (by endocytosis, phagocytosis etc.) or adsorb the pharmaceutical composition particles at a faster rate than the competing dissolution process. The particles should be large enough to allow for the cells to engulf or adsorb the particles and deliver them to the desired target tissue before complete dissolution of the particle. Furthermore, the concentration of the pharmaceutical composition should be kept higher than the saturation solubility of the composition so that the particle is able to remain in the solid state during engulfment, adsorption, or pinocytosis.

Other cells can be used to deliver the the pharmaceutically active compounds to a subject. Any cell type may be used in the present invention so long as it is capable of uptake of the active compound into the intracellular compartment of the cultured cells, attachment of particles of the active compound to the periphery of such cells, or a combination of intracellular uptake and attachment to the cell surface. Examples of other types of cells include: red blood cells, muscle cells, bone marrow and bone cells, vascular cells, organ tissue cells and neuronal cells. Such other cells can be isolated by techniques known to those skilled in the art.

Any method to load particles of pharmaceutically active compounds to cells can be used with the requirement that the method does not destroy or otherwise make the cells non-useful for administration to a subject. For example, site-specific delivery of the particle via a biorecognition molecule may be used. See, e.g., U.S. Patent Publication No. US 2003/0092069, incorporated herein by reference, which discloses the site-specific delivery of genes via a hollow nanoparticle. Other methods of loading the ex-vivo cells include electroporation, sonoporation, and other mechanical means that disrupts the cell membrane (sonication, for example) and enables insertion of solid particulate into the cells. Ultrasound was successfully used by Zamitsyn and Prausnitz (Zarnitsyn V G, Prausnitz M R. Physical parameters influencing optimization of ultrasound-mediated DNA transfection. Ultrasound Med Biol. 2004 April; 30(4):527-38) to transiently disrupt cell membranes and thereby facilitate the loading of DNA into viable cells. Other mechanical procedures are well-known to those experienced in the art, and are included as part of this disclosure. Chemical methods of transiently destabilizing cell membranes is also well known. Transfection reagents contain surface active and include 293Fectin™ Transfection Reagent and Lipofectamine™, both products of Invitrogen Corporation (Carlsbad, Calif.). Another example of a surfactant used to transfer DNA into cells is the SAINT™ reagent from Synvolux Therapeutics B. V. L. J. (Groningen, The Netherlands), which is based on a pyridinium surfactant.

The ex-vivo cells are nurtured in a cell culture medium or other isolating system known to those skilled in the art. Examples of such media are Alserver's Solution, Ames' Medium, Eagle's Basal Medium, CHO (Chinese Hamster Ovary) cell culture media, Click's Medium, Dulbecco's Modified Eagle's Medium, phosphate-buffered saline, phosphate-buffered dextrose or sucrose, Earle's Balanced Salt Solution, Gene Therapy Medium-3, Gey's Balanced Salt Solution, Glasgow Minimum Essential Medium, Hanks' Balanced Salt Solutions, Hybridoma Media, Iscove's Modified Dulbecco's Medium, Krebs-Henseleit Buffer with sugars, Leibovitz Media (L-15), M16 Medium, McCoy's Medium, MCDB, MDBK (Madin-Darby Bovine Kidney), MDCK (Madin-Darby Canine Kidney), Medium 199, NCTC, Ham's Media (e.g., Nutrient Mixture F-10), Coon's Modified Ham's Medium, RPMI, and others such as those listed in Biochemicals & Reagents for Life Science Research, Sigma-Aldrich Co. (St. Louis, Mo., USA). The purpose of the culture so described may be for the purpose of simple storage without loss of cells, or for cell expansion, by appropriate addition of growth factors, cytokines, and nutrients, to encourage cell expansion. Such expansion would minimize the number of times that a patient would have to be prepared for removal of cellular samples.

The loaded cells can be administered intravenously, intramuscularly, subcutaneously, intradermally, intra-articularly, intrathecally, epidurally, intracerebrally, by buccal administration, rectally, topically, transdermally, orally, intranasally, by pulmonary route, intraperitoneally, intra-opthalmically, retro-orbitally, or through any procedure that can be used for delivery of particle-loaded cells to the mammalian subject. The step of administering can be by bolus injection, by intermittent infusion, or by continuous infusion.

The amount of cells and method of delivery will be determined by skilled clinicians. Various factors will affect the cellular concentration and method of delivery including, but not limited to, the type of cells used, the sex, weight and age of the subject to be treated, the type and maturity of the disease or disorder to be treated, the pharmaceutical agent loaded in the cells, and so on.

Certain viruses and bacteria can be taken up by phagocytic cells and continue to remain within these cells. However, cells loaded with the drug particles are effective in treating such infections because the drug is concentrated in the phagocytic cells, and the infecting organism is exposed to much larger amounts of the drug thereby killing the organism. Furthermore, after perfusing into infected tissues, acid-solubilizable particles dissolve due to lower pH levels within the phagocytic cells thereby releasing concentrations of the drug. A concentration gradient is formed with higher concentrations of the pharmaceutical composition within an endosomal body of the phagocytic cells and lesser concentrations outside the endosome. Thus, the contents of the particles within the macrophage are released into the surrounding tissue for ameliorative purposes. Over time, free viral and bacterial organisms residing in the surrounding tissue are exposed to the drug at concentrations higher than what is typically able to be delivered through administration of the free drug, not so encapsulated.

While specific embodiments have been illustrated and described, numerous modifications come to mind without departing from the spirit of the invention and the scope of protection is only limited by the scope of the accompanying claims.

What is claimed is:
1. A method for the preparation and the delivery of small particles of therapeutically active agents to a mammalian subject in need thereof comprising:
(i) collecting phagocytic cells from a mammalian donor,
(ii) nurturing the phagocytic cells in a cell culture medium to which is added a pharmaceutical composition comprising substantially carrier-free particles of one or more therapeutically active agent(s), thereby facilitating phagocytic uptake of the particles by the phagocytic cells so as to form loaded cells; and
(iii) administering an effective amount of the loaded cells formed by phagocytic uptake of the particles by the phagocytic cells to said mammalian subject.

2. The method of claim 1, wherein the step of administering the cells comprises the step of delivering the cells to a target tissue of the mammalian subject.

3. The method of claim 1, wherein the step of administering comprises the step of administering the cells intravenously, intramuscularly, subcutaneously, intradermally, intra-articularly, intrathecally, epidurally, intracerebrally, buccally, rectally, topically, transdermally, intranasally, via the pulmonary route, intraperitoneally, intraopthalmically or combinations thereof.

4. The method of claim 1, wherein the cells are selected from the group consisting of macrophages, monocytes, granulocytes, neutrophils, basophils, eosinophils, dendritic cells and combinations thereof.

5. The method of claim 1, wherein the step of collecting the cells comprises the step of isolating the cells.

6. The method of claim 5, wherein the step of collecting the cells is performed by a cell separator or apheresis device.

7. The method of claim 2, wherein a portion of the particles do not dissolve prior to delivery to the target tissue.

8. The method of claim 1, wherein the composition has a concentration of particles above a saturation solubility of the agent(s).

9. The method of claim 1, wherein the agent(s) is/are poorly water soluble.

10. The method of claim 1, wherein the nurturing the cells step is carried out over a period of up to 24 hours.

11. The method of claim 1, wherein the pharmaceutical composition further comprises a surfactant.

12. The method of claim 11, wherein the surfactant is selected from the group consisting of anionic surfactants, cationic surfactants, zwitterionic surfactants, nonionic surfactants, surface active biological modifiers, and combinations thereof.

13. The method of claim 1, wherein the particles in the composition are amorphous, semicrystalline, crystalline, or a combination thereof as determined by either differential scanning calorimetry or X-ray diffraction.

14. The method of claim 1, wherein the therapeutic agent is selected from the group consisting of: analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, anorexiants, antacids, antidiarrheals, antidotes, antifolics, antipyretics, antirheumatic agents, psychotherapeutic agents, neural blocking agents, anti-inflammatory agents, antihelmintics, antibiotics, anticoagulants, antidepressants, antiepileptics, antifungals, antihistamines, antimuscarinic agents, antimycobacterial agents, antineoplastic agents, antiprotozoal agents, antiviral agents, anxiolytic sedatives, beta-adrenoceptor blocking agents, corticosteroids, cough suppressants, dopaminergics, hemostatics, hematological agents, hypnotics, immunological agents, muscarinics, parasympathomimetics, prostaglandins, protease inhibitors, radio-pharmaceuticals, sedatives, stimulants, sympathomimetics, vitamins, xanthines, growth factors, hormones, antiprion agents and combinations thereof.

15. The method of claim 14, wherein the antineoplastic agent is selected from the group consisting of: paclitaxel and its derivative compounds, alkaloids, antimetabolites, enzyme inhibitors, alkylating agents, antibiotics, genetic therapy agents, and combinations thereof.

16. The method of claim 1, wherein the therapeutic agent is selected from the group consisting of oligonucleotides and nucleic acids.

17. The method of claim 1, wherein the therapeutic agent is a biologic.

18. The method of claim 17, wherein the biologic is selected from the group consisting of proteins, polypeptides, carbohydrates, polynucleotides, nucleic acids and combinations thereof.

19. The method of claim 18, wherein the protein is an antibody selected from the group consisting of polyclonal antibodies, monoclonal antibodies and combinations thereof.

20. The method of claim 1, wherein the pharmaceutical composition is a dispersion that is sterilized prior to nurturing with the phagocytic cells.

21. The method of claim 9, wherein the therapeutically active agent is administered to treat genetically acquired or inherited diseases.

22. The method of claim 21, wherein the genetically acquired or inherited disease is selected from the group consisting of sickle-cell anemia, Burkitt lymphoma, Gaucher disease, hemophilia A, chronic myeloid leukemia, Niemann-Pick disease, paroxysmal nocturnal hemoglobinuria, porphyria, thalassemia, breast and ovarian cancer, colon cancer, small-cell lung carcinoma, malignant melanoma, multiple endocrine neoplasia, neurofibromatosis, pancreatic cancer, polycystic kidney disease, prostate cancer, retinoblastoma, tuberous sclerosis, Von Hippel-Lindau syndrome, Crohn's disease, cystic fibrosis, type 1 diabetes, glucose galactose malabsorption, Wilson's disease, Zellweger syndrome, genetically acquired deafness, Pendred syndrome, Best disease, genetically acquired glaucoma, gyrate atrophy of the choroid and retina, Rett syndrome, adrenal hyperplasia, congenital adrenoleukodystrophy, autoimmune polyglandular syndrome, Cockayne syndrome, diastrophic dysplasia, ataxia telangiectasia, atherosclerosis, long QT syndrome, Williams syndrome, asthma, DiGeorge syndrome, immunodeficiency with hyperIgM, severe combined immunodeficiency, Alport syndrome, male pattern baldness, Fanconi anemia, Hartnup's Disease, Kartagener's Syndrome, lysosomal storage diseases, and pyruvate dehydrogenase deficiency.

* * * * *

UNITED STATES PATENT AND TRADEMARK OFFICE
CERTIFICATE OF CORRECTION

PATENT NO. : 8,333,959 B2
APPLICATION NO. : 11/148453
DATED : December 18, 2012
INVENTOR(S) : Kipp et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 529 days.

Signed and Sealed this
Twenty-first Day of February, 2023

Katherine Kelly Vidal
*Director of the United States Patent and Trademark Office*